United States Patent
Lanier et al.

(10) Patent No.: US 7,297,549 B2
(45) Date of Patent: *Nov. 20, 2007

(54) METHOD OF DETERMINING MEASUREMENT BIAS IN AN EMISSIONS MONITORING SYSTEM

(75) Inventors: William Steven Lanier, Durham, NC (US); Glenn England, Monarch Beach, CA (US)

(73) Assignee: General Electric Company, Schenectady, NY (US)

( * ) Notice: Subject to any disclaimer, the term of this patent is extended or adjusted under 35 U.S.C. 154(b) by 785 days.

This patent is subject to a terminal disclaimer.

(21) Appl. No.: 10/092,678

(22) Filed: Mar. 6, 2002

(65) Prior Publication Data

US 2003/0082822 A1    May 1, 2003

Related U.S. Application Data

(63) Continuation of application No. 09/682,900, filed on Oct. 31, 2001, now Pat. No. 7,029,920.

(51) Int. Cl.
*G01N 1/00* (2006.01)
*G01N 1/10* (2006.01)
*G01N 1/22* (2006.01)
*B32B 5/02* (2006.01)
*B32B 27/04* (2006.01)

(52) U.S. Cl. .................. 436/175; 73/1.01; 73/1.02; 73/23.31; 422/62; 422/83; 422/84; 422/85; 422/86; 422/87; 422/88; 422/89; 422/91; 422/92; 422/93; 422/94; 422/95; 422/96; 422/97; 422/98; 436/155; 436/158; 436/159; 436/116; 436/117; 436/118; 436/122; 436/133; 436/134; 436/136; 436/174; 436/178; 436/181

(58) Field of Classification Search ............... 73/1.01, 73/1.02, 23.31; 422/62, 83–98; 436/155, 436/158, 159, 116, 117, 118, 122, 133, 134, 436/136

See application file for complete search history.

(56) References Cited

U.S. PATENT DOCUMENTS 3,043,145 A    7/1962    Hoffman (Continued)

OTHER PUBLICATIONS

H. Izumi. Japanese Patent Application Kokai: Sho 51-3289. Disclosure date: Jan. 12, 1976.*

*Primary Examiner*—Brian Sines
(74) *Attorney, Agent, or Firm*—Hunton & Williams LLP

(57) ABSTRACT

A method of determining bias in a measurement of a constituent concentration level in a sample gas is provided. The method comprises establishing a sample gas flow from an emission stream into a sample gas line of an emissions monitoring system. The method further comprises removing water from the sample gas flow and cooling the sample gas flow to a temperature below about 41° F. to produce a cooled, dried sample gas flow. The constituent concentration level is then determined for the cooled, dried sample gas flow. The method further comprises introducing a span gas having a known span gas constituent concentration level into the sample gas flow to form a combined sample and span gas flow, the span gas being introduced at a desired span gas flow rate. The method still further comprises removing water from the combined sample and span gas and cooling the combined sample and span gas to a temperature below about 41° F. to produce a cooled, dried, combined sample and span gas flow. A combined sample and span gas constituent concentration level is then determined for the cooled, dried, combined sample and span gas flow. The method also comprises determining a measurement bias using the known span gas constituent concentration level, the sample gas constituent concentration level and the combined sample and span gas constituent concentration level.

6 Claims, 4 Drawing Sheets

U.S. PATENT DOCUMENTS

| | | | |
|---|---|---|---|
| 3,977,836 A * | 8/1976 | Matsuda et al. | 436/113 |
| 4,073,619 A * | 2/1978 | Lawson | 73/863.11 |
| 4,073,866 A * | 2/1978 | Yamaki et al. | 423/405 |
| 4,161,883 A | 7/1979 | Laird et al. | |
| 4,165,630 A | 8/1979 | Felder et al. | |
| 5,610,835 A | 3/1997 | Dominguez et al. | |
| 5,621,213 A * | 4/1997 | Barshad | 250/373 |
| 5,894,083 A | 4/1999 | Hiraoka et al. | |
| 6,094,968 A | 8/2000 | Scheufler et al. | |
| 6,155,210 A * | 12/2000 | Lindman | 122/7 R |
| 2003/0082821 A1 * | 5/2003 | Lanier et al. | 436/118 |

* cited by examiner

METHOD OF DETERMINING MEASUREMENT BIAS IN AN EMISSIONS MONITORING SYSTEM

This application is a continuation of prior application Ser. No. 09/682,900 filed Oct. 31, 2001 now U.S. Pat. No. 7,029,920.

BACKGROUND OF THE INVENTION

This invention relates to the measurement of air pollutant emissions from gas turbines, boilers, process heaters, furnaces and other combustion sources. More particularly, the invention relates to a continuous emission monitoring method and system that minimizes bias in the measurement of air pollutant emissions.

Power plants and other users of combustion sources such as gas-fired turbines are required to keep emissions of certain exhaust constituents at or below specified levels. Continuous emission monitoring systems (CEMS) are required in order to assure on a continuous basis that the mandated levels are maintained. Over time, however, improved methods of minimizing emissions have evolved and emissions standards have become more stringent. CEMS systems are therefore required to consistently measure lower and lower concentrations of pollutant emissions.

As the maximum allowable concentrations of air pollutants have decreased, the effects of bias in CEMS measurements have become more and more significant. One example of particular interest is in the measurement of nitrogen oxides concentration. Nitrogen oxides emitted from combustion sources are defined as the sum of nitric oxide (NO) and nitrogen dioxide ($NO_2$). The combination of the two is referred to as $NO_x$. The majority of $NO_x$ from many combustion sources is NO with about 2% to 5% as $NO_2$. For gas turbines, $NO_2$ typically represents 5 to 15% of the total $NO_x$. Under certain circumstances, however, in gas turbines equipped with $NO_x$ control systems, $NO_2$ may represent as much as 50% of total $NO_x$. In most cases, the relative amounts of NO and $NO_2$ need not be determined. Nevertheless, the presence of a greater or lesser amount of $NO_2$ can have an impact on bias in the measurement system used to determine the total $NO_x$ concentration.

Current CEMS systems are subject to a number of sources of bias with respect to $NO_x$ measurement. The resulting biases become more significant as the total $NO_x$ concentration level gets smaller. Recent technology improvements have resulted in combustion systems with $NO_x$ emissions in the range of 1 to 10 ppm. Environmental Protection Agency (EPA) regulations place upper limits on the sum of all measurement bias and constituent interference effects. Bias effects in the systems now in use may prevent these systems from meeting the accuracy requirements that go along with the measurement of smaller concentrations.

SUMMARY OF THE INVENTION

There is accordingly a need for a CEMS that minimizes bias in the measurement of emission constituent concentration levels generally and $NO_x$ concentration levels in particular. There is also a need for a CEMS that provides for routine monitoring of the remaining bias in the system.

The present invention provides an emissions monitoring system for monitoring constituent concentration levels in an emission stream flowing through a combustion source exhaust stack. The system comprises a sampling device configured and positioned for extraction of sample gas from the emission stream in the stack. A chamber is positioned adjacent the stack and defines a chamber interior. The system includes an arrangement for maintaining in the chamber interior a temperature above a dew point temperature of the sample gas. At least one sample gas line is in fluid communication with the sampling device. At least a portion of the sample gas line is disposed in the chamber interior. The system includes an arrangement for removing particulate matter from the sample gas. The arrangement for removing particulate matter is disposed adjacent the stack and is in fluid communication with the at least one sample gas line. The system also includes an arrangement for removing water from the sample gas. This arrangement is also in fluid communication with the at least one sample gas line. The system further comprises at least one analyzer in fluid communication with the at least one sample gas line, each of the at least one analyzer being configured for determination of a concentration level of a constituent in the sample gas.

An illustrative embodiment of the present invention provides an emissions monitoring system for monitoring constituent concentration levels in an emission stream flowing through a combustion source exhaust stack. The system comprises a sampling device configured and positioned for extraction of sample gas from the emission stream in the stack. A chamber is positioned adjacent the stack and defines a chamber interior. The system includes an arrangement for maintaining in the chamber interior a temperature above a dew point temperature of the sample gas. At least one sample gas line is in fluid communication with the sampling device. At least a portion of the sample gas line is disposed in the chamber interior. The system also includes an arrangement for removing particulate matter from the sample gas. The arrangement for removing particulate matter is disposed in the chamber interior and is in fluid communication with the at least one sample gas line. The system comprises an $NO_2$-converter in fluid communication with a first one of the at least one sample gas line. The $NO_2$ converter is operable to convert $NO_2$ gas in the sample gas to NO gas and is disposed in the chamber interior. The system also comprises an arrangement for removing water from the sample gas, the arrangement being in fluid communication with the at least one sample gas line. The system further comprises a first analyzer in fluid communication with the first one of the at least one sample gas line. The first analyzer is configured for determination of an NO concentration level in the sample gas.

One aspect of the invention provides an emissions monitoring system for monitoring constituent concentration levels in an emission stream flowing through a combustion source exhaust stack. The system comprises a sampling device configured and positioned for extraction of sample gas from the emission stream in the stack. A chamber is positioned adjacent the stack, the chamber defining a chamber interior. A chamber heater is disposed in the chamber interior. The system further comprises at least one sample gas line in fluid communication with the sampling device. At least a portion of the sample gas line is disposed in the chamber interior. A filter is disposed adjacent the stack, the filter being in fluid communication with the at least one sample gas line so that the sample gas passes through the filter. The filter removes particulate matter from the sample gas to produce a filtered sample gas. The system also includes a dryer disposed adjacent the chamber. The dryer is in fluid communication with the at least one sample gas line and has a dryer intake for receiving the filtered sample gas and a dryer exit for returning dried filtered sample gas to the at least one sample gas line. The dryer is configured for removing water from the filtered sample gas and for effectively lowering the dew point of the filtered sample gas. The system also comprises at least one analyzer in fluid communication with the at least one sample gas line. Each of the at least one analyzer is configured for determination of a concentration level of a constituent in the dried filtered sample gas.

The dryer in a monitoring system according to the invention may be disposed in the chamber interior. A monitoring system according to the invention may comprise a conduit disposed intermediate the dryer exit and the at least one analyzer, at least a portion of the at least one sample gas line being disposed within the conduit for maintaining the dried filtered sample gas at a temperature above 32° F.

An embodiment of the invention provides a method of monitoring a concentration level of $NO_x$ in an exhaust stream from a combustion source. The method comprises capturing sample gas from the exhaust stream using a sample gas probe. $NO_2$ in the sample gas is converted to NO by passing the sample gas through a catalytic $NO_2$ converter. The method includes removing water from the sample gas by passing the gas through a dryer and determining a sample gas NO concentration level. The step of converting $NO_2$ is performed at a temperature above a dew point temperature of the sample gas.

Another illustrative embodiment of the invention provides a method of monitoring a concentration level of $NO_x$ in an exhaust stream from a combustion source. The method comprises capturing sample gas from the exhaust stream using a sample gas probe and cooling the sample gas to a temperature below about 250° F. but above a dew point temperature of the sample gas. The method further comprises removing particulate matter from the sample gas and converting $NO_2$ in the sample gas to NO by passing the sample gas through a catalytic $NO_2$ converter. The method still further comprises cooling the sample gas to a temperature sufficient to cause the water in the sample gas to condense out of the sample gas. A sample gas NO concentration level is then determined. The step of converting $NO_2$ is performed at a temperature above the dew point temperature of the sample gas and precedes the step of cooling the sample gas to a temperature sufficient to cause water in the sample gas to condense out of the sample gas.

In yet another embodiment of the invention, a method of monitoring a concentration level of a constituent in an exhaust stream from a combustion source comprises capturing sample gas from the exhaust stream using a sample gas probe. The method further comprises cooling the sample gas to a temperature below about 250° F. but above a dew point temperature of the sample gas and removing particulate matter from the sample gas. Water is removed from the sample gas by passing the sample gas through a dryer. The method further comprises measuring a sample gas flow rate downstream of the dryer and determining a sample gas constituent concentration level. A span gas having a known span gas constituent concentration level is introduced into the sample gas to form a combined sample and span gas flow. The method includes measuring a combined sample and span gas flow rate downstream of the dryer. A combined sample and span gas constituent concentration level may then be determined. The method also includes determining an overall system bias using the known span gas constituent concentration level, the sample gas constituent concentration level and the combined sample and span gas constituent concentration level.

Other objects and advantages of the invention will be apparent to one of ordinary skill in the art upon reviewing the detailed description of the invention.

BRIEF DESCRIPTION OF THE DRAWINGS

The present invention can be more fully understood by reading the following detailed description of presently preferred embodiments together with the accompanying drawings, in which like reference indicators are used to designate like elements, and in which.

DETAILED DESCRIPTION OF THE INVENTION

Figure 1:
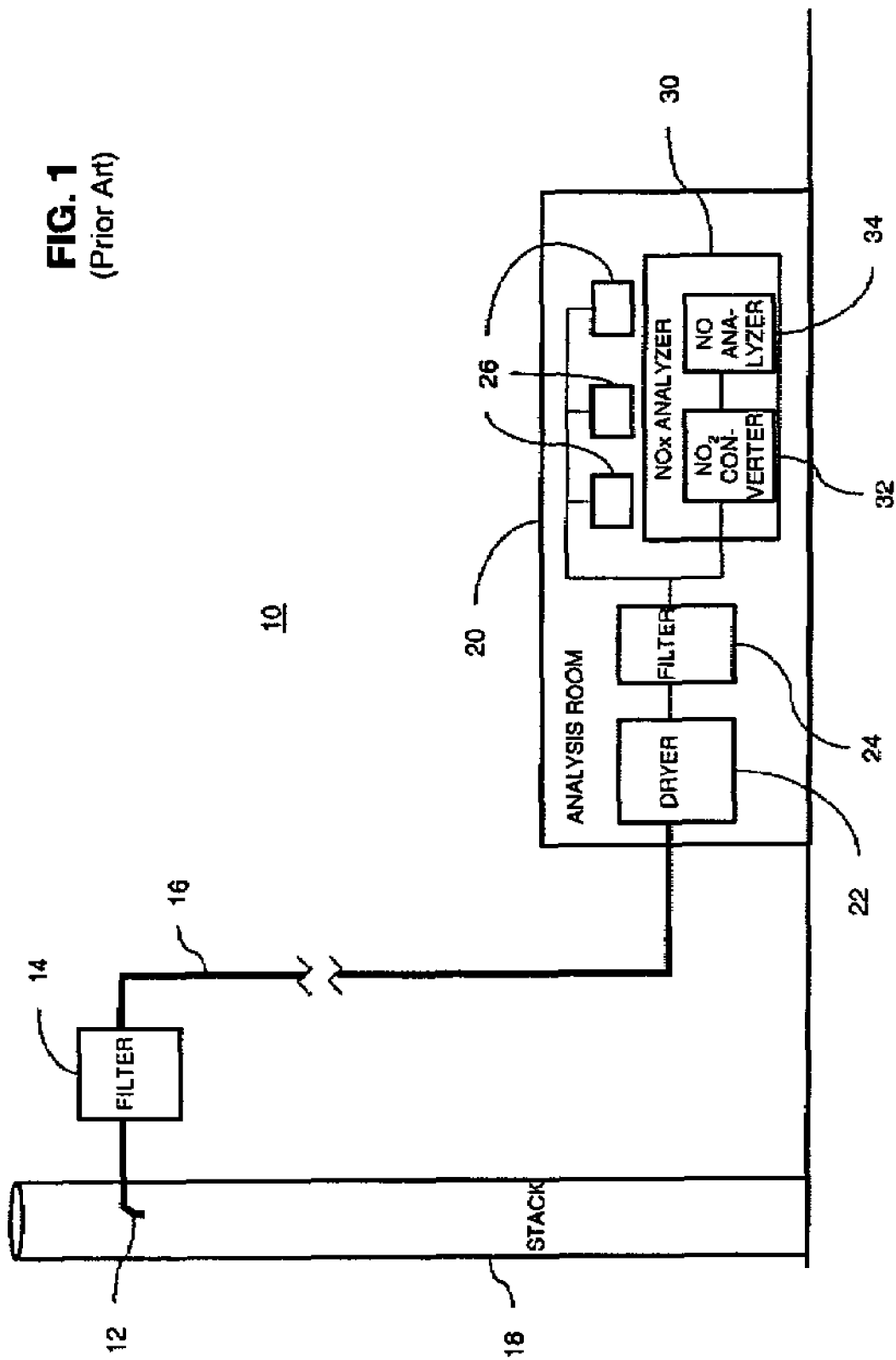
FIG. 1 is a block diagram of a prior art continuous emission monitoring system.

The present invention provides an emissions monitoring system that minimizes bias effects in the capture and analysis of $NO_x$ emissions. The invention also provides a method for routinely monitoring the system to identify changes in measurement bias. FIG. 1 is a schematic illustration of a typical prior art emissions monitoring system 10. In the system 10, multiphase exhaust emissions are drawn from a stack 18 using a sampling device 12. At the outlet of the sampling device 12, the emissions are passed through a filter 14 to remove large particulate matter on the order of 7 microns or greater.

The resulting sample gas and any remaining particulate matter are then passed through a heated sampling line 16 to a CEMS analysis room 20. The analysis room 20 is typically a small ground level building, trailer or mobile sampling van that houses the analyzers for the various types of emissions that must be assessed. Such a building is typically carefully climate controlled. Upon entering the analysis room 20, the sample gas is passed through a dryer 22, which is typically a refrigeration condenser with condensate traps for removal of water from the sample gas. The sample gas is then passed through a second filter 24 which removes approximately 99.99% of all particles greater than 0.5 microns. The sample gas is then split so that a portion of the gas proceeds into a $NO_x$ analyzer 30. The remainder of the gas is passed to other CEMS analyzers 26, which assess concentration levels of such constituents as oxygen ($O_2$), carbon monoxide (CO) and sulfur dioxide ($SO_2$).

The $NO_x$ analyzer 30 includes an $NO_2$ converter 32 and an NO analyzer 34. In general, $NO_x$ concentration levels need only be determined as a total of NO and $NO_2$ levels. Available $NO_x$ analyzers are only able to determine the concentration of NO in a sample gas. It is therefore necessary to convert any $NO_2$ in the gas to NO. This is accomplished using the $NO_2$ converter 32. The converter 32 may be a separate module but is often an integral part of the analyzer. After conversion of the $NO_2$ to NO, the analyzer 34 determines the concentration of NO in the sample gas.

The system 10 is calibrated by closing off the sampling device 12 and injecting calibration gases upstream of the first filter 14. The calibration gases, which are sometimes referred to as span gases, include known concentration levels of the emission gases of interest. The calibration gases are then passed through the same sequence as the sample gases in order to determine if the system 10 is properly measuring the sample gas constituents.

The above-described emissions monitoring system 10 has a number of sources of bias relative to the measurement of $NO_x$ concentration. Chief among these is the potential for low measurements due to the presence of interfering species in the gas sample. Flue gases from most combustion sources typically contain about 8 to 30% water. For example, because $NO_2$ is water soluble (as opposed to NO, which is not water soluble), condensation and subsequent removal of liquid water from the sample gas can result in the removal of significant amounts of $NO_2$. As a result, it is imperative that condensation be minimized. Typical prior art systems have therefore required significant measures to assure that the water in the sample gas does not condense out prior to the passage of the gas through the dryer 22.

These measures generally depend on keeping the sample gas at a temperature above the temperature at which water would condense out (i.e., the dew point). Stack gases from which the sample gases taken are generally at elevated temperatures. For a simple cycle gas turbine, stack gases are typically on the order of 1200° F. The stack gases must be cooled to a temperature that will not damage system components but must be kept above the dew point to prevent condensation. While the dew point of these gases may vary depending on composition, it is typically about 200° F. or higher. To keep the sample gas above this temperature, the filter 14 must be heated. Moreover, the sample gas must be transported from the sampling device 12 and the filter 14 to the dryer 22 using a heated sample line 16. The sample line 16 is heated using electrical heating elements imbedded in the line. These heating elements maintain the sample gas at a constant temperature of approximately 250° F. Because the dryer 22 is remote from the stack 18, the heated line 16 may be hundreds of feet long.

Heating and maintaining the sample line 16 is expensive. Moreover, there are often localized failures of the electrical heating elements. Such failures can result in water condensation in the line 16 and consequent loss of $NO_2$ from the sample gas.

$NO_x$ measurement bias can also result from the conversion of other nitrogen-containing species to NO by the $NO_2$ converter 32. One example where this might occur is in a Selective Catalytic Reduction (SCR) system subject to ammonia slip. Such a system could result in an inadvertently high $NO_x$ concentration determination because of the conversion of ammonia to NO. This type of bias is highly dependent upon the catalytic material used in the converter 32.

An additional potential for bias in CEMS systems stems from the fact that the stack gases are composed of a mixture of gases, typically $N_2$, $O_2$, $H_2O$, $CO_2$, CO, and $NO_x$. Emissions analyzers are typically calibrated by injecting a span gas with a known concentration of the key constituent (potentially a trace species such as NO) in a background of molecular nitrogen ($N_2$). The electronic components of the analyzer are adjusted such that instrumental response agrees with the known span gas concentration. When the analyzer is used to determine the concentration of the key constituent (such as NO) in an actual flue gas, the sample background matrix will be much more complex than the $N_2$ in the span gas. The differences in background gas composition can result in potentially significant measurement bias known as a matrix effect.

Figure 2:
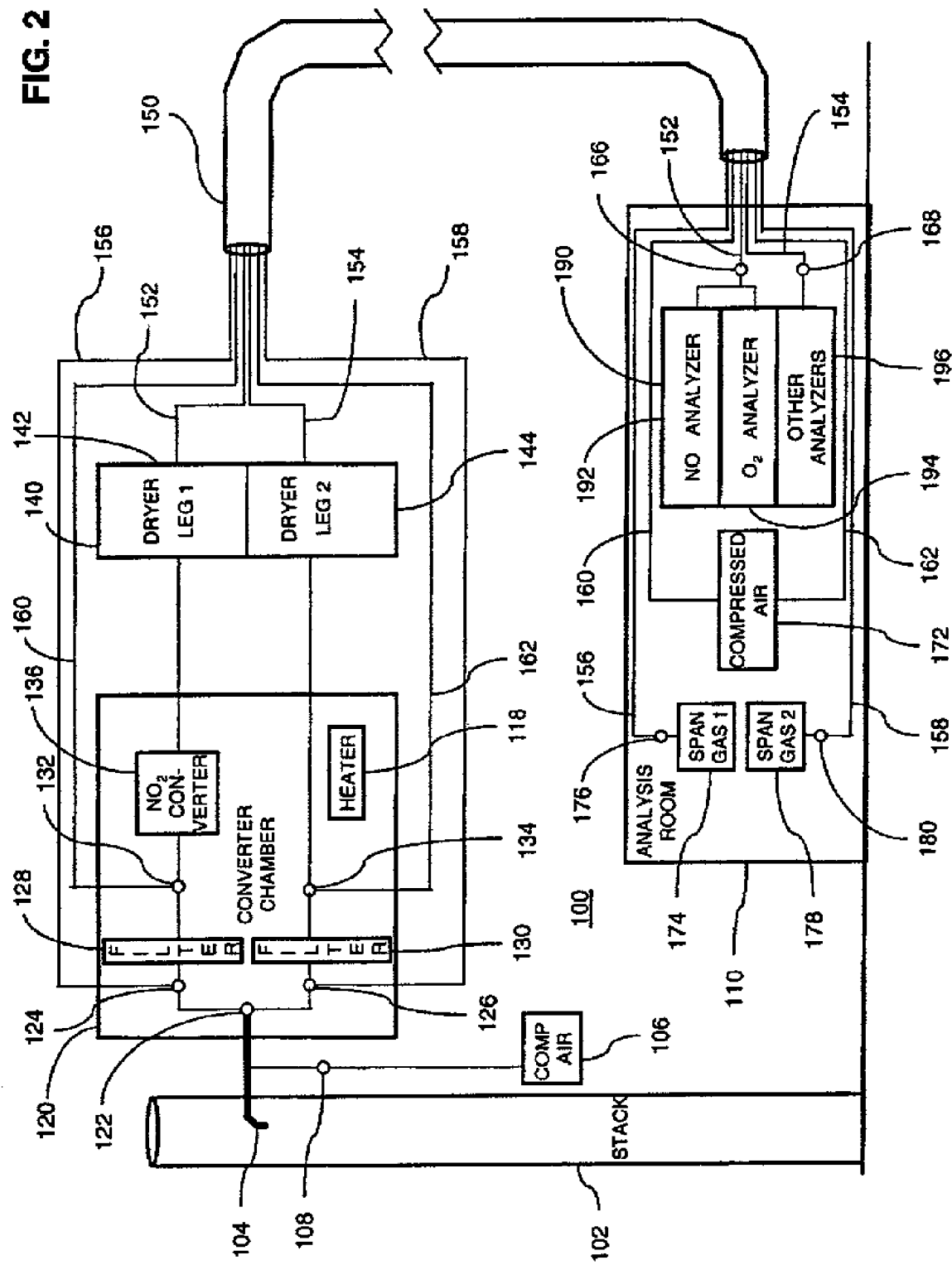
FIG. 2 is a block diagram of a continuous emission monitoring system according to an embodiment of the present invention.

The present invention provides a monitoring system wherein the above described biases are significantly reduced or eliminated. The system also allows remaining biases to be quantified. FIG. 2 is a schematic illustration of a CEMS 100 according to the present invention. The CEMS 100 uses a fundamentally different approach to $NO_x$ concentration measurement in that it uses an $NO_2$ converter 136 that is specifically designed and configured for use on hot, wet gas samples. The $NO_2$-converter 136 is housed in an environmentally controlled converter chamber 120 that is situated in close proximity to the stack 102 from which the sample gas is withdrawn. After passage through the $NO_2$ converter 136, the sample gas is passed through a refrigeration dryer 140 where water in the sample gas is condensed out and removed. The sample gas is then passed through a conduit 150 to an analysis room 110 and an NO analyzer 192. Because the $NO_2$ in the gas has already been converted to NO and the gas has already been dried, the conduit 150 need only be configured to maintain the sample gas at temperatures above freezing. The CEMS 100 also includes subsystems for back-flushing the filters in the system, for calibrating the system and for a dynamic spiking process that allows assessment of interference and other biases remaining in the system.

An illustrative embodiment of the invention will now be discussed in more detail. The CEMS 100 uses a sampling device to withdraw sample emission gas from a stack 102. The sampling device may be configured for passive extraction of exhaust gases or for active extraction through the use of an applied vacuum. In embodiments of the invention, the sampling device 104 is a dual-annulus, air-cooled probe that extends into the stack interior. In this configuration, compressed air flows through an annular outer jacket of the probe 104 to cool the sample gas from stack temperatures of about 1000-1300° F. to a temperature that is just above the dew point of the gas, which is typically in the range from about 190° F. to 250° F. The gas temperature of the probe outlet 122 will typically be in a range from about 250° F. to about 350° F. Higher temperatures may be used depending on the materials in the system. Such temperatures, may however, tend to degrade system components formed from low tolerance materials such as TEFLON™. It will be understood by those having ordinary skill in the art that reduced gas temperature and the relatively low temperature of the inner liner of the probe 104 also lower the tendency for CO in the gas to oxidize to $CO_2$, which can bias the measurement of CO concentration in the gas. It will also be understood that other cooling arrangements could be used without departing from the scope and spirit of the invention. Such arrangements could include the passage of other fluids through the jacket, dilution cooling or the use of refrigeration.

The flow rate of the compressed air through the outer jacket of the probe 104 is controlled in such a way as to maintain a desired gas temperature at the outlet 122 of the probe 104. A compressed air source 106 provides compressed air through a valve 108 controlled by a controller electrically connected to a thermocouple at the probe outlet 122. The thermocouple provides a sample gas temperature to the controller which opens or closes the valve 108 as appropriate to maintain the desired temperature.

The probe 104 extends out through the wall of the stack 102 and into the converter chamber 120. In one exemplary configuration, the converter chamber 120 may be mounted on or adjacent the stack 102. The converter chamber 120 may be weatherproofed and may be heated as described hereinafter. At the exit 122 of the probe 104, the sample gas flow is split between two sample lines 152, 154. A first line 152 is used to carry sample gas that will be used to assess $NO_x$ and $O_2$ concentration levels. A second line 154 is used to carry sample gas that will be used to assess concentration levels of other compounds such as CO, $CO_2$ and $SO_2$.

It will be understood by those of ordinary skill in the art that the probe 104 may have multiple sampling tips at different locations in the stack 102 to provide a representative sample of the exhaust stream. Alternatively, multiple separate probes may be used. The sample gas from the various locations may be analyzed separately or as a single overall sample.

The sample gas flow is split in order to avoid the potential for biasing the measurement of other constituents. For example, when sample gas is passed through the $NO_2$ converter 136, there is a strong potential for creation of trace levels of CO by the catalytic reaction of $NO_2$ on the carbonaceous surface of the converter 136. As will be understood by those having ordinary skill in the art, reducing $NO_2$ to NO liberates an oxygen atom that may be attached to a carbon atom on the converter surface. The resulting CO molecule can be released to the gas stream and bias the CO emission measurement. This problem is avoided by splitting the sample gas into two streams, only one of which is passed through the $NO_2$ converter 136. Only the sample gas that is not passed through the converter 136 is used to assess CO concentration. Splitting the flow also provides the advantage of minimizing the required size (i.e., flow capacity) of the $NO_2$ converter, which reduces system cost.

The first and second sample gas lines 152, 154 are passed through first and second span gas valves 124, 126, respectively. As will be discussed in more detail hereafter, the span gas valves 124, 126 are used during the calibration and dynamic spiking processes to introduce gases with known constituents into the system. Filters 128, 130 are disposed across the sample gas lines 124, 126 to remove solid particles from the sample gas. These filters 128, 130 are configured to remove 99% of all particles greater than about 2.0 microns in size. It will be understood that the two filters 128, 130 could be replaced with a single filter positioned upstream of where the flow sample gas flow is split. It will also be understood that the filters 128, 130 could be housed separately from the converter chamber 120, in which case the sample gas lines would pass from the probe 104 to the filter housing(s), then to the converter chamber 120. This approach would acquire additional heating measures to assure that the sample gas remains above its dew point.

Just downstream of the filters 128, 130, the sample gas lines 152, 154 are passed through back-flush valves 132, 134. These valves 132, 134, which may be, for example, three-way valves with one input, are connected to compressed air lines 160, 162, which in turn are connected to a compressed air supply 172. Using these valves 132, 134, compressed air may be introduced into the gas sample lines 124, 126 to back-flush the filters 128, 130 and the sample probe 104.

The first sample gas line 152 is connected to the $NO_2$ converter 136, which is also disposed within the heated converter chamber 120. The $NO_2$ converter 136 used in the CEMS 100 is designed for operation in high temperature, wet gas streams. As used herein, high temperature refers to temperatures above 250° F. and a wet gas stream is one having a dew point above about 5° C. (41° F.). The converter 136 uses carbon or carbon/molybdenum to establish the catalytic reaction and convert $NO_2$ to NO. Typically, the converter 136 does not include stainless steel. This reduces the potential for reaction with ammonia, thereby reducing or eliminating bias in the $NO_x$ measurement due to the presence of ammonia in the gas. An exemplary converter that is suitable for use in the invention is the model CG-2H converter produced by MProducts Analysentechnik GmbH. This converter is capable of operation at temperatures up to about 635° F. The converter is capable of handling gas flow rates of 3 L/min., which is suitable for use in the invention.

The converter chamber 120 and all components disposed therein are maintained at a temperature of at least 250° F. to prevent condensation from occurring in the sample gas lines 152, 154 and, in particular, to prevent condensation from occurring upstream of the $NO_2$ converter 136. This may be accomplished with a chamber heater 118 using electric heating coils, a forced air heating system, steam or any other arrangement suitable for heating the interior of the converter chamber 120.

Both sample gas lines 152, 154 pass out of the converter chamber 120 to a dryer 140, which is preferably disposed adjacent the converter chamber 120. The dryer 140 is divided into a first leg 142 wherein water is removed from the $NO_x$ sample gas line 152 and a second leg 144 wherein water is removed from the second sample gas line 154. The dryer 140 is a refrigerated unit that reduces the temperature of the gas to about 40° F., thereby causing the water in the sample gas to condense out. Because the dryer 140 is downstream of the $NO_2$ converter, the first dryer leg 142 does not need to be configured to minimize subsequent contact of the gas with the liquid water. The sample gas at this point contains no significant amount of $NO_2$ that could otherwise be lost through water contact. The result is a simpler dryer configuration, which significantly reduces the cost of the dryer 140. As an additional benefit, increased contact between the sample gas and liquid water in the dryer 140 has the effect of removing certain reactive species such as ammonia from the sample gas. The process of removing moisture from the sample gas results in the sample gas being saturated at the temperature of the gases when they leave the cooler.

The second dryer leg 144 may be configured differently from the first dryer leg. In particular, if sample gas from the second sample gas line 154 is to be used to determine the concentration level of a water soluble compound such as ammonia or $SO_2$, the second dryer leg may be configured to minimize contact of the sample gas with the condensate.

After passage through the dryer 140, the sample gas lines 152, 154 are routed to an analysis room 110. Both the converter chamber 120 and the dryer 140 are in close proximity to the stack 120 but the analysis room 110 is typically relatively remote. In the CEMS 100 of the present invention, the sample gas lines 152, 154 are routed along with two compressed air lines 160, 162 and two span gas lines 156, 158 through a conduit 150 to the analysis room 110. Unlike the lines in prior art systems, the conduit 150 need not be heated to a high temperature (e.g., 250° F.) to keep the sample gases above the dew point of the gas. The conduit 150 need only be configured to assure that the sample gas temperature remains above freezing. This may generally be accomplished through the use of insulation or in some cases a warming system. In either case, the cost of installation and maintenance of the conduit 150 is significantly lower than for the heated lines of prior system. Moreover, there is no concern over biases introduced due to localized failures of a heating system.

The analysis room 110 houses an analyzer bank 190 comprising a variety of analyzers for different types of emissions. The analysis room 110 may be a room within the main building of a plant, a separate ground level building, a ground level trailer or other facility. Because some analyzers may be subject to variation as a result in changes to ambient conditions, the primary requirement for the analysis room is that it include the capability to maintain precise environmental control.

The analyzer bank 190 of the CEMS 100 includes an NO analyzer 192, an $O_2$-analyzer 194 and a bank of other analyzers 196. The other analyzers may include one or more units for determination of concentration levels of $SO_2$, CO, $CO_2$ or other sample gas constituents. Upon entering the analysis room, the first sample gas line 152 is passed through a first mass flow meter 166 and the second gas flow line 154 is passed through a second mass flow meter 168. After passage through the second gas flow meter 168, the second gas flow line 154 is passed to the bank of analyzers 196 where it is split into as many separate lines as are necessary for analysis by the various constituent analyzers. The first gas flow line 152 is split into two lines, one of which proceeds into the NO analyzer 192 and the other of which proceeds into the $O_2$ analyzer in, for example, the manner described above. These analyzers are substantially similar to the analyzers used in prior art systems and may include any analyzer suitable for taking measurements in compliance with regulatory specifications.

It will be understood that the sample gas from the first gas flow line 152 may also be used to assess other constituents, such as $CO_2$ that would not be affected by passage through the converter 136. As a result, the first gas flow line 152 may be further split to provide sample gas to other analyzers.

In the system 100, the analysis room 110 also houses a compressed air source 172 and two span gas sources 174, 178. As previously mentioned, the compressed air source 172 provides compressed air for use in back-flushing the filters 128, 130 and the sampling probe 104. The span gas sources 174 and 178 provide gases having known constituent concentrations for use in calibration of the system 100. The first span gas source 174 is connected to a first span gas line 156, which passes through a first flow meter/controller 176. Similarly, the second span gas source 178 is connected to a second span gas line 158, which passes through a second flow meter/controller 180. Both span gas lines 156, 158 are then passed out of the analysis room 110 and through the freeze-protected conduit 150 to the converter chamber 120. The first span gas line 156 is connected to the first sample gas line 152 at the first span gas valve 124 and the second span gas line 158 is connected to the second sample gas line 154 at the second span gas valve 126. The span gas valves 124, 126 are configured to selectively close off the sample gas lines 152, 154 from the sample probe 104 and allow span gas from the first and second span gas sources 174, 178 to pass through the first and second sample gas lines 152, 154, respectively.

Span gases allow the calibration of the system 100 using gases having known concentration levels of constituents of interest. It will be understood by those having ordinary skill in the art each of the span gas sources 176, 178 may be used to introduce any of multiple span gas variations into the system 100. The span gas sources 176, 178 can also be used to introduce a substantially inert gas such as $N_2$ for use in zeroing the analyzers 192, 194, 196 (i.e., assuring that the analyzers register zero when their respective constituents are not present in the gas flowing through the system).

In the CEMS 100, the compressed air source 172 and the span gas sources 174, 178 are positioned in the analysis room 110 primarily as a matter of convenience. It will be understood by those having ordinary skill in the art that these sources may be placed elsewhere without departing from the scope of the invention.

The CEMS 100 may include an automated data processing system (not shown) for use in controlling the various components of the system and for data acquisition, storage and processing. The automated data processing system may provide access to the CEMS 100 via modem or other network connection.

It will be understood by those of ordinary skill in the art that, although the system 100 is referred to as a continuous emissions monitoring system, the system 100 can be operated either continuously or at random or predetermined intervals.

Figure 3:
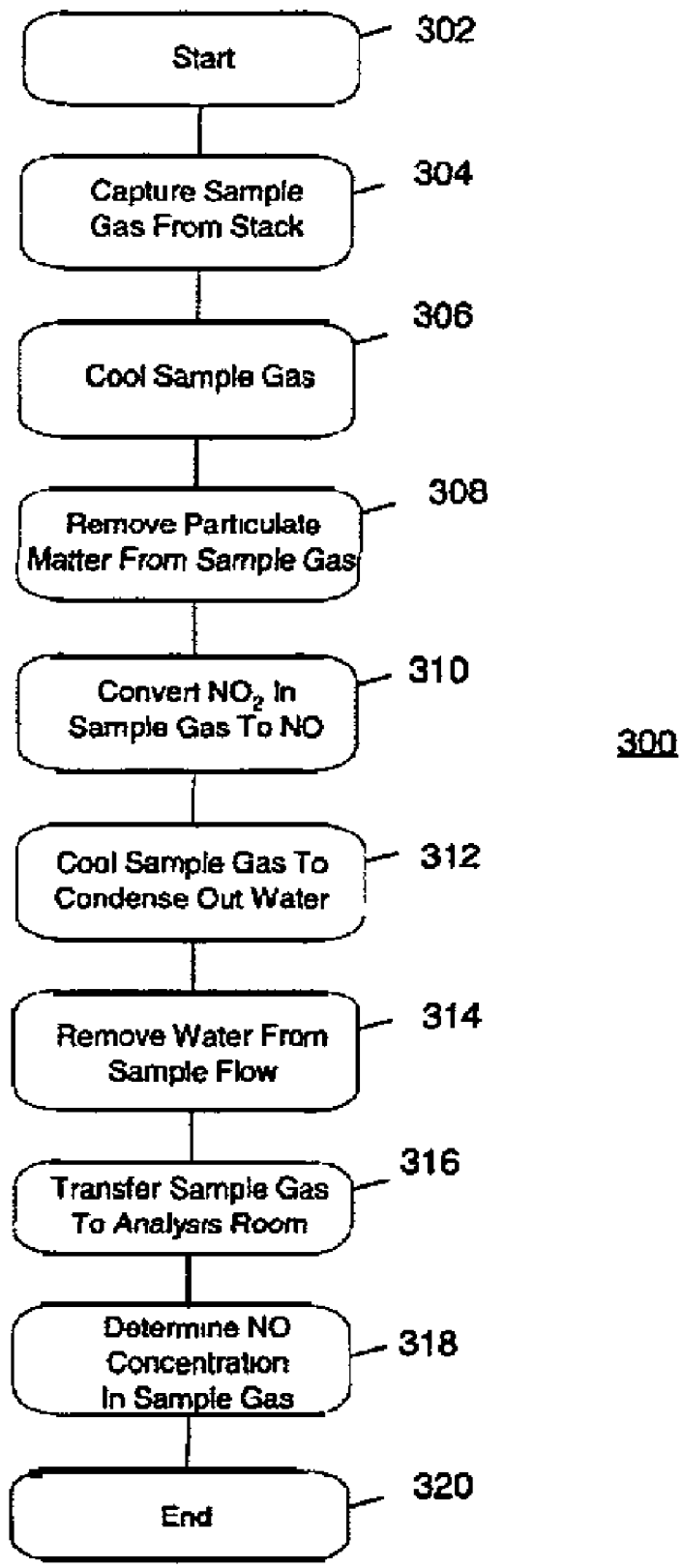
FIG. 3 is a flowchart of the steps of a method of monitoring a constituent level according to an embodiment of the invention.

A method 300 of monitoring $NO_x$ emissions using the CEMS 100 is illustrated by the flow chart in FIG. 3. The method 300 begins at step 302. At step 304 the sample gas is captured from the stack 102 by the sampling probe 104. This may be accomplished in either an active or passive manner. At step 306, the sample gas is cooled to a temperature above the dew point of the gas and at least a portion is introduced into the sample gas line 152. At step 308, particulate matter is removed from the sample gas by passing the gas through a filter 128. $NO_2$ in the sample gas is then converted to NO by passage of the gas through the $NO_2$ converter 136 at step 310. The sample gas is kept at a temperature above the sampling gas dew point during steps 308 and 310. At steps 312 and 314, water in the sample gas is condensed out and removed using the refrigerated dryer 140. At step 316, the sample gas is passed to the analysis room 110 through the freeze-protected conduit 150. At step 318, at least a portion of the sample gas passed through the $NO_2$ converter is analyzed by the NO analyzer to determine the concentration of NO in the sample gas. The method 300 ends at step 320.

In order to comply with continuous emission monitoring guidelines, the analyzers of a CEMS must be regularly calibrated. With respect to $NO_x$ emissions, this may be accomplished by the CEMS 100 of the present invention by the separate introduction into the system of a zeroing gas having a substantially zero NO gas concentration and a span gas having a known concentration of NO. The zeroing gas is preferably $N_2$ and the span gas is preferably a mixture of $N_2$ and NO. The amount of NO in the span gas is typically on the order of the full scale measurement capability of the system 100. The response of the NO analyzer 192 may be automatically adjusted to conform to the concentration of the span gas. Calibration may be accomplished several times per day and any calibration drift recorded and reported to the EPA.

Similar calibration procedures may be used with respect to the other analyzers in the system 100 as well. The span gas introduced through the second span gas line 158 may be used for single emission constituents in an otherwise inert gas or may include multiple emission constituents.

Although these calibration procedures provide some measure of the accuracy of the analyzers, they do not directly provide a means of assessing interference and other bias effects remaining in the system 100. The system 100 provides for the use of dynamic spiking of the sample gas flows to assess these effects. The basic approach is to spike the sample gas such that there is a known step function increase in the concentration level of a particular constituent. For example, without closing off the sampling probe 104, the first span gas line 156 may be used to introduce a span gas having a known concentration level of NO into the sample gas flow at a known flow rate. This allows for a direct check on the existence and magnitude of any biases in the measurement of NO concentration.

To maintain the accuracy of the dynamic spiking method, the flow rate of and concentration level in the span gas should be known with a high degree of precision. The flow rate of the sample gas before and after addition of the span gas should also be measured precisely.

The dynamic spiking method may be described using the following example. A gas turbine is operating with a stack $NO_x$ concentration of 9 ppm. The sample flow is preferably dynamically spiked in such a way as to approximately double the $NO_x$ concentration. This may be accomplished in a manner that has minimal impact on the concentration of other sample gas constituents. To accomplish both objectives, a spiking span gas with approximately 90 ppm $NO_2$ may be introduced into the sample gas flow. The balance of the spiking gas may be $N_2$. The flow rate of the spiking gas is set to be approximately 1/10 the flow rate of the sample gas flow. This results in an $NO_x$ concentration in the mixed gas stream that is double that of the sample gas alone. This also results in a 10% dilution of the other sample gas constituents.

The mass flow meters/controllers 176, 180 in the span gas lines 156, 158 may be used to determine the actual flow rates of the spiking gas. The mass flow meters 166, 168 in the sample gas lines 152, 154 may be used to determine the actual flow rates of the sample gas plus the spiking gas. A significant feature of the system 100 is that the mass flow meters will be processing cool, dry gases. This significantly enhances the reliability of these instruments and improves the confidence level in their measurements.

In operation, the step function addition of $NO_2$ to the sample stream challenges all components of the sampling system. The sum of all biases introduced by losses in the filter (e.g., through absorption), the converter, the dryer or the transfer lines and any inaccuracy or bias in the NO analyzer itself can be assessed by comparing the differential between the $NO_x$ concentration of the spiked gas and the $NO_x$ concentration of the unspiked gas to the known concentration in the span gas. Importantly, this assessment is made with all of the actual sample gas constituents included in the sample gas.

A further feature of the dynamic spiking system is that the sample flow passed through the $NO_2$ converter 136 is piped to both the NO analyzer 192 and the $O_2$ analyzer 194. During dynamic spiking, the $O_2$ concentration in the sample gas will be decreased by a known percentage. (In the example above, the $O_2$ concentration would be reduced by 10%.) The oxygen measurement provides a direct check on proper operation of the mass flow meters/controllers used to determine the relative split of sample flow and spiking flow.

Figure 4:
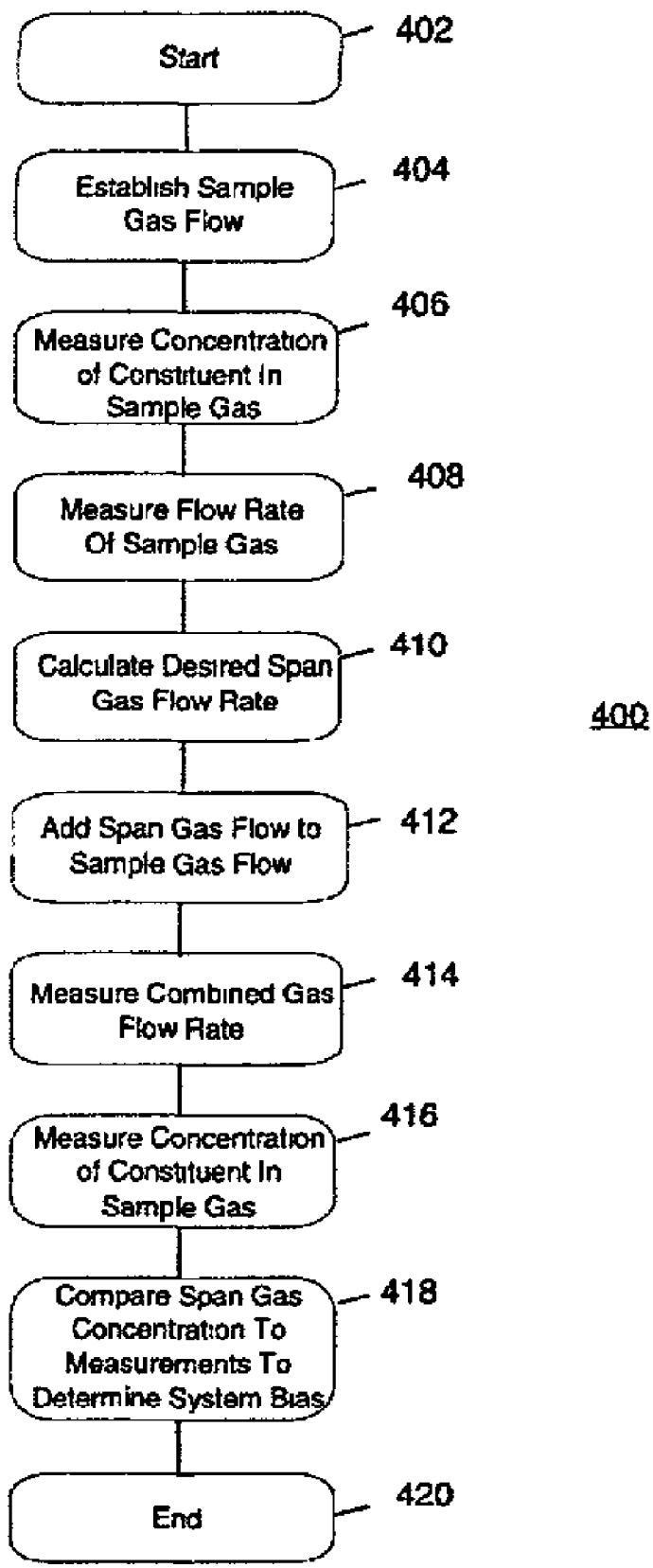
FIG. 4 is a flowchart of the steps of a method of assessing system bias according to an embodiment of the invention.

The steps in a dynamic spiking method are illustrated by the flow diagram in FIG. 4. The method begins at step 402. At steps 404 and 406, a sample gas flow into the system 100 is established and the concentration of a constituent of interest is determined. These steps are carried out in substantially the same manner as previously described in the method 300 of continuously monitoring $NO_x$ emissions. If the constituent of interest is not a $NO_x$ component, however, the steps would be carried out using the second sample gas line 154 and the step of passing the sample gas through the $NO_2$ converter 136 would be eliminated. At step 408, flow rate of the sample gas and concentration of the key constituent, such as $NO_2$, are measured, such as by using one of the two flow rate meters 166, 168 and the appropriate analyzer, such as the NO analyzer 192. Based on the measured sample gas flow rate and an approximate desired concentration level of the constituent, a spiking flow rate of a span gas with a known constituent concentration may be calculated at step 410. Span gas at the desired flow rate is then added to the sample gas flow at step 412. At step 414, the flow rate of the combined sample gas and span gas is measured. The appropriate analyzer is then used to determine the concentration level of the constituent in the combined gas at step 416. A comparison is then made at step 418 between the known concentration of the constituent in the span gas and the measured difference between the analyzer results for the sample gas alone and the sample gas plus the span gas. This comparison provides a quantitative indication of the overall system bias. The method ends at step 420.

As previously noted, the accuracy of the dynamic spiking method is dependent on the accuracy of the mass flow measurements. It will be understood by those of ordinary skill in the art that the presence of water, $O_2$ or $CO_2$ in a sample gas can cause a flow rate measurement bias in flow meters calibrated using a span gas without these constituents. It will also be understood that a simple algorithm can be used to correct the mass flow rate if the relative percentages of these constituents in the sample gas are known. In the present invention, the water concentration remaining in the sample gas can be determined from the temperature of the sample gas as it leaves the refrigerated dryer 140. The $O_2$ and the $CO_2$ concentrations in the sample gas are determined by the $O_2$ and $CO_2$ analyzers, respectively. With these concentrations known, the mass flow correction algorithm can be used to correct the mass flow values obtained from the flow rate meters 166, 168 in the sample gas lines 152, 154, thus enhancing the accuracy of the dynamic spiking method.

It will be understood that the above-described dynamic spiking method may be used on either leg of the system (i.e., using sample gas in sample gas line 152 or sample gas line 154). In this manner, the performance of all analyzers in the CEMS 100 may be assessed.

The dynamic spiking system of the present invention also provides a methodology for routinely demonstrating that the overall CEMS system 100 is in compliance with the accuracy dictates of the EPA or other such regulatory body or simply for internal purposes. Both the calibration and dynamic spiking processes of the present invention may be conducted manually or through the assistance of an automatic data processing system.

While the foregoing description includes many details and specificities, it is to be understood that these have been included for purposes of explanation only, and are not to be interpreted as limitations of the present invention. Many modifications to the embodiments described above can be made without departing from the spirit and scope of the invention, as is intended to be encompassed by the following claims and their legal equivalents.

What is claimed is:

1. In an emissions monitoring system, a method of determining bias in a measurement of a constituent concentration level in a sample gas, the method comprising:
    establishing a sample gas flow from an emission stream into a sample gas line;
    removing water from the sample gas flow and cooling the sample gas flow to a temperature below about 41° F. to produce a cooled, dried sample gas flow;
    determining the constituent concentration level for the cooled, dried sample gas flow;
    introducing a span gas having a known spa gas constituent concentration level into the sample gas flow to form a combined sample and span gas flow the span gas being introduced at a desired span gas flow rate;

removing water from the combined sample and span gas and cooling the combined sample and span gas to a temperature below about 41° F. to produce a cooled, dried, combined sample and span gas flow;

determining a combined sample and span gas constituent concentration level for the cooled, dried, combined sample and span gas flow; and determining a measurement bias using the known span gas constituent concentration level, the sample gas constituent concentration level and the combined sample and span gas constituent concentration level.

2. A method according to claim 1 further comprising the steps of:

measuring a sample flow rate of the cooled, dried sample gas flow; and measuring a combined gas flow rate of the cooled, dried, combined, sample and span gas flow.

3. A method according to claim 2 further comprising the steps of:

determining a concentration level of a secondary constituent in the cooled, dried sample gas;

correcting the sample flow rate using the secondary constituent concentration level in the cooled, dried sample gas flow;

determining a concentration level of the secondary constituent in the combined, cooled, dried span and sample gas flow; and correcting the combined gas flow rate using the secondary constituent concentration level in the combined cooled, dried sample and span gas flow.

4. A method according to claim 3 wherein the secondary constituent is one or more of water, $O_2$ and $CO_2$.

5. A method according to claim 1 further comprising the step of:

calculating the desired span gas flow rate using a desired combined sample and span gas constituent concentration level, the sample gas flow rate and the span gas constituent concentration level.

6. A method according to claim 5 wherein the desired combined sample and span gas constituent concentration level to calculated using a predetermined ratio of span gas constituent concentration level to combined sample and span gas constituent concentration level.

* * * * *